United States Patent [19]

Lassmann et al.

[11] Patent Number: 5,832,709

[45] Date of Patent: Nov. 10, 1998

[54] METHOD OF CHECKING THE YARN PROFILE ASSOCIATED WITH A YARN PIECING OPERATION IN AN OPEN-END SPINNING MACHINE

[75] Inventors: Manfred Lassmann, Nettetal; Heribert Mertens, Willich, both of Germany

[73] Assignee: W. Schlafhorst AG & Co., Germany

[21] Appl. No.: 771,639

[22] Filed: Dec. 20, 1996

[30] Foreign Application Priority Data

| Dec. 20, 1995 | [DE] | Germany | 195 47 545.3 |
| Nov. 28, 1996 | [DE] | Germany | 196 49 314.5 |
| Nov. 28, 1996 | [DE] | Germany | 196 49 329.3 |

[51] Int. Cl.[6] ................................................ D01H 13/26
[52] U.S. Cl. .......................... 57/263; 57/264; 57/265; 73/160
[58] Field of Search ................................ 57/263, 264, 265; 73/160

[56] References Cited

U.S. PATENT DOCUMENTS

| 3,751,981 | 8/1973 | Jernigan et al. | 73/160 |
| 4,489,544 | 12/1984 | Morita et al. | 57/263 X |
| 4,660,365 | 4/1987 | Raasch | 57/263 |
| 4,774,673 | 9/1988 | Aemmer | 73/160 X |
| 4,817,425 | 4/1989 | Ueda et al. | 73/160 |
| 4,821,502 | 4/1989 | Bur Sek et al. | 57/263 |
| 4,825,632 | 5/1989 | Raasch et al. | 57/264 |
| 5,124,928 | 6/1992 | Aemmer | 73/160 X |
| 5,511,371 | 4/1996 | Kaufmann | 57/264 |
| 5,537,811 | 7/1996 | Pidoux et al. | 57/264 |
| 5,557,916 | 9/1996 | Messmer et al. | 57/264 X |

FOREIGN PATENT DOCUMENTS

| 0 291 710 B1 | 4/1988 | European Pat. Off. . |
| 24 09 882 B2 | 2/1974 | Germany . |
| 2725105 | 12/1978 | Germany | 57/263 |
| 34 27 357 A1 | 7/1984 | Germany . |
| 4030100 | 4/1992 | Germany | 57/263 |
| 2164961 | 4/1986 | United Kingdom | 57/263 |

OTHER PUBLICATIONS

Abstract from Autocoro Manual entitled Piecing Tester (ASP1), W. Schlafhorst AG & Co., Nov. 1991.

Primary Examiner—William Stryjewski
Attorney, Agent, or Firm—Kennedy Covington Lobdell & Hickman, LLP

[57] ABSTRACT

A method includes dividing a yarn into various sections with reference to the pieced yarn section, with each section being characteristic of the piecing process. A yarn profile in each section is measured and evaluated against criteria specific to each section, whereby a yarn defect and its position on the yarn are determined and from which the cause for the defect is determined. The pieced yarn section is also divided into three subsections and each subsection is measured and evaluated against certain subsection criteria for the detection of fluff, trash accumulation and fiber sloughing.

20 Claims, 7 Drawing Sheets

METHOD OF CHECKING THE YARN PROFILE ASSOCIATED WITH A YARN PIECING OPERATION IN AN OPEN-END SPINNING MACHINE

FIELD OF THE INVENTION

The present invention relates to a method for checking a yarn profile following a yarn piecing operation in an open-end spinning machine and, more particularly, to a method for determining deviations of the yarn profile from a standard profile derived from a section of the yarn unaffected by the piecing operation and evaluating for yarn defects the deviations with respect to quality threshold values.

BACKGROUND OF THE INVENTION

With regard to conventional open-end spinning machines, when the spinning of yarn has been interrupted by a yarn break or by a yarn package exchange, a yarn piecing operation must be performed in order to restart the yarn spinning process. In the spinning process, the yarn previously spun is reinserted into the spinning machine to restart the yarn spinning. The point of juncture between the previously spun yarn and the fibers which attach thereto when the spinning process is restarted represents a pieced section of the yarn which differs in its profile and structure from the profile and structure of a normally spun yarn that is drawn from an ongoing and continuous spinning operation. If the yarn profile of the pieced section and adjacent sections do not meet certain quality criteria, the yarn can present a troublesome risk to subsequent yarn processing steps.

For this reason, it is known to monitor the profile of the yarn that is spun after a piecing operation to determine whether the yarn profile deviates from a predetermined yarn profile representing minimum quality standards. For example, from U. S. Pat. No. 4,825,632 which is hereby incorporated by reference, and from European Patent Publication EP 0 291 710 B1, it is known to monitor in an open-end spinning machine the yarn profile following a piecing operation. In this process, the respective diameter values of the pieced section itself, which extends over a length corresponding to a rotor groove circumference, and the yarn sections located before and after the pieced section, each which respectively are at least approximately the length of the pieced section, are automatically measured relative to the longitudinal yarn axis of the yarn sections and the measured values are electronically stored. These values, collected in a memory device in the course of the measuring process, are communicated to a comparator which compares these values with a value formed from average values. The comparison result is compared with the previous comparison result and, in case of a deviation from a predetermined standard, a corrective change in the piecing operation is made, for example, by correcting the yarn feed.

In accordance with the teaching of this prior art reference, the comparison of the actual measured values is performed to detect both short thick and short thin places, i.e., extreme deviations of the yarn profile from the normal yarn, which either cause a significant reduction in the strength of the yarn (thin places) or which are visible in the subsequent textile fabric in spite of their short longitudinal length (thick places). To the extent that long faulty yarn sections are analyzed, an average value formation of the yarn signals within the entire diagnostic area of the yarn is performed, and this average value is compared with a threshold value. Because of this technique, successive thick and thin places can complement each other with the effect that the detection of long defects is limited to only those situations in which such a compensation does not occur or remains within limits. Furthermore, in this prior art technique, it is not possible to determine the exact location of long thick and long thin places, particularly in respect to the pieced yarn section and the connection point therein. It is therefore not possible to determine with any particularity the exact cause of an observed defect so that, even if a defect is detected, the wrong conclusion and, possibly, the wrong corrective measure will be taken in changing the piecing operation parameters in accordance with the teaching of this reference.

As long as the deviations in the yarn profile of the pieced section or in its close vicinity are the result of settings of the piecing carriage, it is generally possible to prevent the repetition of the same defect by changing one or more of the piecing operation parameters. However, there are also situations in which the reason for the defect is not a result of a setting of the piecing carriage like, for example, so-called "fluff," which consists of fiber accumulation that remains in the rotor from the preparation of the actual piecing process, i.e., fiber which is not drawn off by the low pressure prevailing in the spinning chamber before the actual piecing process is started. This fiber or trash accumulation results from either the rotor cleaning process or from the combing process of the fiber tuft, the latter being performed for the purpose of always having an evenly combed out fiber tuft for the piecing process, regardless of the down time of the spinning station. For assisting the removal of such residues from the rotor, a valve bore in the conduit plate, for example, is opened prior to feeding of the fibers which are to be connected to the yarn end of the returned yarn by spinning, through which air is aspirated from the outside because of the low pressure prevailing in the spinning chamber and by means of which normally a sufficiently strong suction flow is generated. Fibers can remain in the rotor, however, due to an incomplete opening of the valve bore or due to special shapes of the rotor or certain conduit plate embodiments, depending on the material and the spinning conditions. Such fluff is incorporated into the pieced section and leads to a local thickening or increase in the diameter of the yarn, often with an adjoining thin place resulting from local overtwisting of the yarn. The latter is caused by the twist wandering off into the downstream adjacent area of the yarn because of the thickening formed by the fluff Depending on the fiber material, spinning conditions, and the draw-off nozzle, it is also possible for fiber sloughing to occur in the area of the pieced section, which leads to the same practical defect in the pieced section.

If such fluff or trash accumulation is incorporated into the yarn, or fiber sloughing occurs, a corresponding evaluation of a yarn defect may occur in accordance with the prior art with the result that a change in the piecing operation parameters is performed. However, since the yarn defect was not caused by a deviation from a controlled variable of the piecing operation, a correction of the controlled variable results in an incorrect setting for piecing or spinning and, therefore, can propagate new yarn defects.

In summary, in the course of checking the yarn profile of a running yarn during and following piecing in an open-end spinning machine as taught by the prior art, it is possible that an absolute value measurement of the yarn profile and a subsequent comparison with a threshold value can lead to a false evaluation of the yarn profile, as can the formation of an average value wherein all values are added up over a lengthy section and are then divided by the number of the values. These checking methods provide neither a determination of the position of the defect nor its type, so that a directed removal of the cause of the defect is not possible.

OBJECT AND SUMMARY OF THE INVENTION

It is therefore an object of the present invention to further improve yarn piecing operations over the state of the prior art and thereby improve the overall quality of yarn produced.

It is a further object of the present invention to identify a plurality of sections of the yarn which have characteristics resulting from the yarn piecing process, to assign section-specific criteria for evaluating the yarn profile within each section as well as over multiple sections, to identify every detected defect with a location on the yarn, and to determine the cause of the defect based on the type of defect and the position of the defect on the yarn, i.e., the section in which the defect occurs.

It is a further object of the present invention to identify a plurality of subsections of the pieced yarn section for evaluating the yarn profile against subsection-specific criteria for the identification of fluff, trash accumulation and sloughing.

A first featured method of the present invention includes: determining with a sensor associated with a spinning machine deviations of a yarn profile from a normal yarn profile and storing the deviations in a computer; identifying with the computer for evaluation purposes in response to the sensor a plurality of yarn sections of the measured yarn, each section having a characteristic resulting from the piecing operation, evaluating yarn defects by evaluating with the computer, beginning at the start of each section, the deviations in each section with respect to section-specific threshold values that are predetermined by permissible deviations from the normal yarn profile; and, determining with the computer the cause of an evaluated defect based upon the type and location of the defect thereby providing information for evaluating possible modification of the piecing operation.

A further characteristic of the first featured method includes determining sectional boundaries based upon the determination, as a reference point, of the connection point which results from the piecing operation, the connection point beginning at the pieced section of the yarn and representing the connection between the returned yarn and the fiber ring of the rotor of the spinning machine in the piecing operation. Preferably, this determination of the connection point includes the detection of a maximum measured yarn diameter within the area of the yarn in which the connection point is expected and then the identification of the first measured yarn diameter occurring before the maximum measured yarn diameter that is less than the standard yarn diameter of the normal yarn profile.

Preferably the identification, or division, of the measured yarn into sections includes the identification of at least five yarn sections including a pieced section and two sections respectively located in front of and behind the pieced section, with the pieced section beginning at the connection point on the yarn resulting from the piecing operation and extending along the yarn from the connection point over a length corresponding to the rotor groove circumference of the spinning machine. Furthermore, the identification of the sections of the measured yarn preferably includes the determination of the length of each section as a function of the geometry of the spinning machine and the yarn parameters.

The evaluation performed in the first featured method of the present invention preferably includes calculating a comparison value for each deviation starting at the beginning of each section for making a comparison thereof with a section-specific threshold value, with the calculation of each comparison value preferably including all deviations occurring in the section prior to and including the deviation for which the comparison value is calculated.

Specifically, the evaluation preferably includes: calculating for each deviation in each section a comparison value comprising the sum of the deviations occurring in the section prior to the deviation for which the comparison value is calculated; calculating the product value of the sum and the number of deviations comprising the sum; and comparing the product value to a predetermined fixed threshold value for each section, whereby a defect is detected if the product value exceeds the threshold value.

Alternatively, or in conjunction therewith, the evaluation also includes: calculating for each deviation in each section a comparison value comprising an average deviation over deviations occurring in the section prior to and including the deviation for which the comparison value is calculated; and, comparing the comparison value to a quotient threshold value arrived at by dividing a predetermined threshold value by the number of deviations averaged in the comparison value, whereby a defect is detected if the comparison value exceeds the quotient threshold value.

Moreover, the first featured method also preferably includes the continuation of each respective evaluation begun in each section into another section independently of the beginning of another evaluation in the other section.

A characteristic of the present invention includes the determination of each threshold value by taking into consideration the required yarn strength in the individual sections and the capability of detecting defects in yarn products during further processing of the yarn.

Furthermore, the comparison values calculated are preferably retained and accumulated in the computer for a plurality of piecing operations, regardless of whether a defect is detected, for detecting yarn tendencies.

Preferably the standard yarn profile is determined from a top yarn which first passes the sensor after the start of the yarn draw-off in the course of the piecing operation and which is unaffected by the piecing operation.

The second featured method of the present invention includes a method for checking the yarn profile of a yarn drawn off an open-end spinning machine following a piecing operation, including the steps of: determining with a sensor associated with the spinning machine deviations of a yarn profile from a normal yarn profile and storing the deviations in a computer; identifying with the computer for evaluation purposes a plurality of subsections of the pieced yarn section with each subsection having characteristics of the pieced section and with the pieced section extending from the connection point on the yarn over a yarn length corresponding to one circumference of a rotor groove of the spinning machine; and making a subsection-specific evaluation of the yarn profile in each subsection for the detection of defects.

Preferably the pieced section is divided into three subsections and the evaluation includes detecting defects by comparing deviations in two subsections that include the boundaries of the pieced section to respective threshold values and by detecting a sequence of flank rises and drops in the deviations in the third subsection located between the two subsections. Moreover, the identification of the subsections preferably includes the determination of the length of the pieced yarn section as a function of the geometry of the spinning machine and the yarn parameters, and the boundaries of the subsections preferably overlap one another.

With respect to the foregoing, the present invention also contemplates the combination of various features and characteristics discussed above for the improvement of the detection of defects in a yarn.

DETAILED DESCRIPTION OF THE PREFERRED EMBODIMENT

A first featured method of the present invention contemplates that, for an exact evaluation of a yarn profile of a yarn drawn off a spinning station after a piecing operation, a division of the yarn into a sufficient number of longitudinal yarn sections must be performed so that the detection of short and long defects within each yarn section is possible, and a sufficiently precise evaluation of the yarn profile of the pieced section and its vicinity is achieved when the yarn is preferably divided into five sections having characteristics resulting from the piecing operation. Since a proper diagnosis for the cause of a defect can depend upon which yarn section the defect occurs in, a correct diagnosis of the cause of the defect can be determined and a directed regulation of the piecing conditions for rapid and effective correction of the defect can be performed in accordance with this first featured method of the present invention.

Specifically, while the determination of the location of a pieced yarn section is determined in accordance with the prior art based on the known yarn travel and the rotor radius, which forms the basic unit length for all pieced sections within a yarn batch, the individual yarn profile of each pieced yarn section produced at the spinning station is individually determined after each piecing operation in accordance with the present invention. Moreover, the yarn is divided into sections having characteristics resulting from the piecing operation by reference to the connection point of the pieced yarn section which is determined for each yarn profile. This process assures a more exact determination of the connection point between the upper yarn and the fiber ring. Moreover, starting from this exact determination of the position of the connection point, the determination of the pieced yarn section, which extends over a length corresponding to the circumference of the rotor groove, is easily and accurately made. This determination in turn defines the exact location of the remaining yarn sections and their boundaries, all of which are determined with reference to the yarn connection point and the pieced yarn section. Of course, the length of the sections which are preferably selected is not always the same, but rather, depends on the geometry of the spinning means and on the yarn parameters which determine the typical structure of an average yarn section, including the longitudinal dimension of defined yarn profile sections and the crosswise dimension thereof, as will be apparent to one of ordinary skill in the art.

Figure 1:
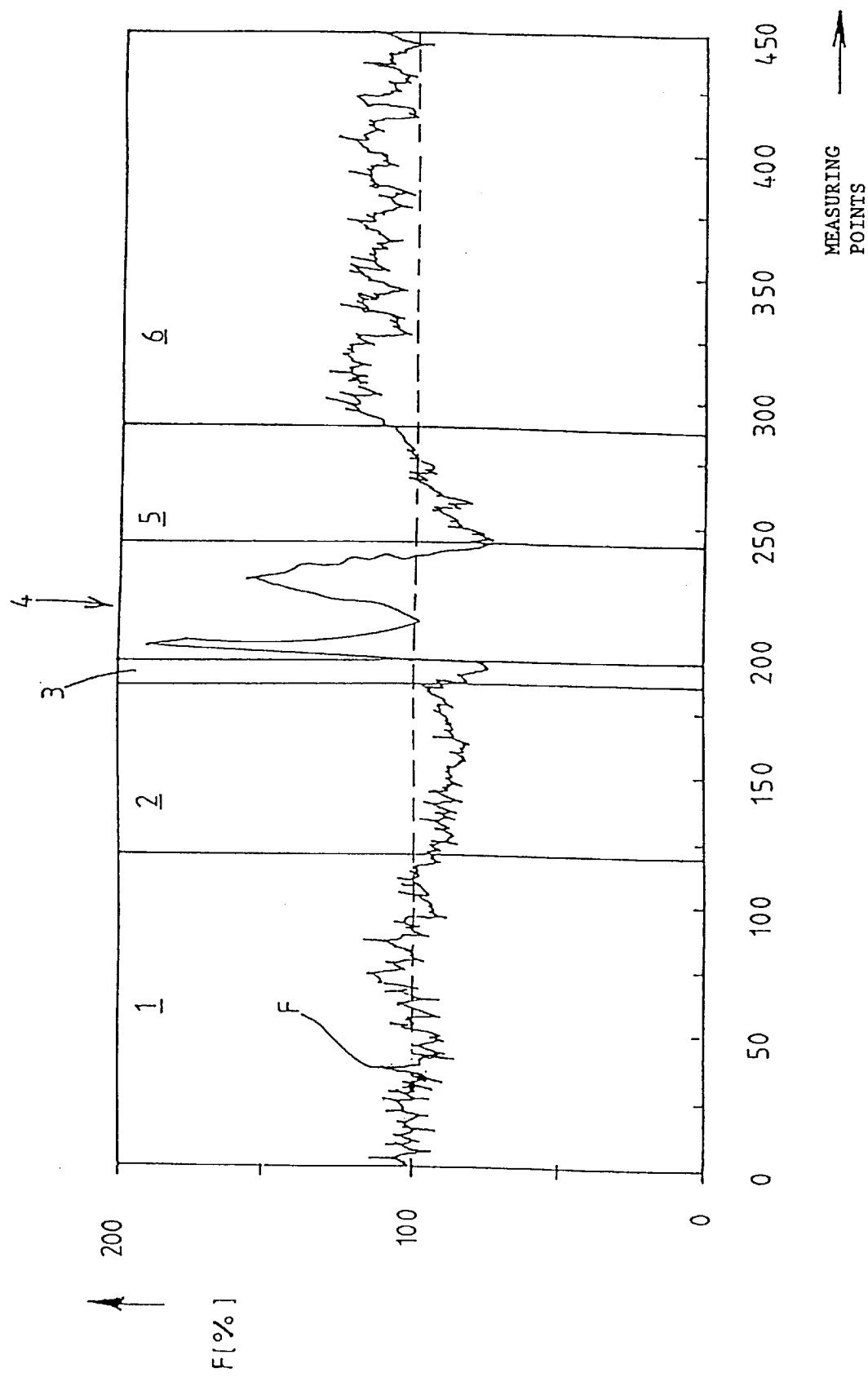
FIG. 1 shows a yarn profile including a division thereof into five sections having characteristics resulting from a piecing operation in accordance with the present invention.

A typical yarn profile is shown in FIG. 1. The yarn profile has been divided for evaluation purposes into five sections including a pieced yarn section 4 and sections 1–3 and 5–6, all of which have typical deviations from a desired yarn profile. Specifically, a yarn diameter deviation in units of percent is plotted against yarn length in units of measuring points. If the yarn length in millimeters is sought for the exact location of a defect, the number of measuring points to the defect is multiplied by the measurement resolution, which in the present case is 2.5 mm and corresponds to the size of the measuring window of the sensor measuring the yarn diameter. Likewise, in place of an absolute extent, each sectional length can be defined by an appropriate number of measuring points because of the fixed distance, or measurement resolution, between the measuring points.

Section 2 which follows the upper yarn section 1 in FIG. 1 shows the characteristic behavior of the yarn in this area: because of the introduction of too great of twisting during piecing, the yarn diameter in this section is reduced. The very narrow section 3 immediately preceding the pieced section 4 is characterized by a repeated, clear drop in the yarn diameter before a very steep rise up into the range of almost 200% of the yarn diameter in the pieced section 4. Section 4 starts at the connection point of the pieced section, the determination of which is described below, and includes one rotor circumference. The drop of the yarn diameter down to a value around 100% in section 4 is just as steep as its rise, and the subsequent measurement peak is less. This is caused by the fact that, on the one hand, at the start of the yarn draw-off during piecing a fiber ring must be present in the rotor groove, so that after overlapping no thin place in the yarn is obtained at the connection point, which would cause reduced strength of the pieced section, and, on the other hand, it is necessary to feed sufficient fibers even during the draw-off of the first yarn length which corresponds to a rotor circumference (pieced section) in order not to result in a very distinctive thin place downstream of the pieced section. These fibers, which are continuously fed during the draw-off of the first fiber ring length, then generate the described second thick place in the pieced section. In the present case this is more weakened than in a desired pieced section and therefore subsequently causes a thin place.

Section 5 immediately follows the pieced section 4 and starts at the end of the first rotor revolution following the connection point. Section 6 follows section 5 and starts at the end of the second rotor revolution following the connection point in the pieced section 4, whereat the yarn diameter lies slightly above the 100% value in the yarn profile shown, which is likely caused by, for example, too great of an amount of fiber being fed as a result of an erroneous setting of the spinning unit.

In order to be able to exactly determine the sectional boundaries following each piecing operation, the position of the connecting point in the pieced yarn section must first be determined as exactly as possible. To accomplish this, after the start of the yarn draw-off in the piecing operation, the first absolute maximum of the yarn diameter value is determined in the area where the connection point is expected.

Starting at this position, the yarn signal is tracked backward in steps of measuring points until a negative standardized diameter deviation is reached. This position plus one measuring point results in the determination of the connection point, since a thin diameter of the yarn is created immediately ahead of the overlap because of the wandering of the twists out of the overlapped area.

The determination of the length of the yarn section takes place, as already mentioned, as a function of, in particular, the spinning means and the yarn parameters. For example, the yarn division represented in FIG. 1 constitutes an average division, wherein the scale for the other sections is predetermined by the length of the pieced yarn section 4 which exactly corresponds to the length of a rotor groove circumference. A changed rotor diameter has an appropriate effect.

It is necessary for the evaluation of the profile of yarn spun to form a scale which is independent of the yarn count. One basis for comparison includes the extent to which the spun yarn deviates in yarn thickness or yarn mass from previously spun upper yarn that is unaffected by the most recent piecing process. Another basis for standardization that can be used, for example, is the value previously measured by the yarn cleaner on the running yarn in the spinning process, or a standard average yarn value formed by means of many measurements.

In the preferred method of the present invention, and as illustrated in FIG. 1, percent value deviations are advantageously employed so that a percent deviation from a standard yarn diameter forms the basis for the yarn signal evaluation and comparison to threshold values. If a certain percent deviation is defined as the threshold value, a conversion of this threshold value into the absolute yarn signal can be calculated by the evaluation device using a standardization factor. Alternatively, the yarn signal representing yarn diameter can be standardized prior to evaluation by means of a factor, wherein the standard yarn reference value, e.g., the upper yarn reference value, represent 100%.

The preferred method of the present invention will be further explained by means of the standardization of measured yarn diameters. Thus, in order to be able to calculate a deviation value which permits evaluation of the pieced yarn with the already present yarn, a standard yarn diameter is first determined based on, for example, measurements of the upper yarn section, which yarn diameter is fixed at 100%. Preferably a yarn section of the upper yarn is located sufficiently from the pieced yarn section to be unaffected by the piecing operation, and this upper yarn section is preferably used to determine a base for standardization of further yarn sections. The upper yarn section, identified by section 1 in FIG. 1, includes the area of the previously spun yarn which is used as the basis for calculating the standard yarn diameter for the yarn profile illustrated therein.

With respect to comparing the yarn diameter measured with the desired yarn profile, as is known from the prior art, short defects are generally detectable, but short defects are not detected if, for example, they do not consistently lie above a threshold value of the yarn diameter deviation (or yarn mass deviation) of the minimum length extension determined for short defects. If, for example, a length of 10 mm has been fixed as the minimum defect length, a single drop of the yarn diameter below the threshold value within this length does not result in detection of a defect. However, this defect can become noticeable in subsequently produced textile fabric or can cause a loss of strength of the yarn during later yarn processing. Moreover, such a defect is not detectable by the prior art average value formation, since the single decrease of the yarn diameter would most likely be compensated for by the remaining yarn sections which contribute to the average value formation of the prior art.

Therefore, in accordance with the first featured method of the present invention, preferably both a sliding average value calculation and an integration of the measured deviation values is performed, and, in both cases, the tendencies of the yarn profile development is determined and localized within the respective yarn sections. Moreover, besides the defects typical for any particular section, it is advantageous to further expand the section-specific evaluation into sections located thereafter in order to detect defects which cover several sections. Thus, preferably, several yarn evaluations are performed simultaneously in defined sections and over each continuous and chronological sequence of sections.

Each calculated average profile deviation for each section and each sequence should be compared after each measurement with a calculated threshold value function. A defective pieced section is then recognized if a calculated averaged profile deviation reaches or exceeds the threshold value of the threshold value function at that measuring point.

The exact determination of threshold values is performed on the basis of experimental values, which can be stored in a data bank and called up as required, and section-specific threshold value determinations for the individual sections will be discussed further below. Still, the exact determination of the threshold values should be individually performed by the operator, taking into consideration the subsequent employment of the yarn. Moreover, since like yarn defects particularly in respect to strength can have different effects in different yarn sections, such differences must be taken into consideration in the course of determining the various section-specific threshold values to be used in accordance with the present invention. Furthermore, the fiber material employed and the future purpose of use of the produced yarn are also important factors in the determination of the threshold values which relate to the size and length of defects in respect to later visual effects of as well as strength requirements of the yarn, as will be apparent to one of ordinary skill in the art.

A preset threshold value having dimensions of centimeter-percent (cm %) is conventionally used for long defects. Thus, the determination of a defect takes place by means of the product of the yarn defect length and the percent deviation of the yarn profile thereof from a preset profile. Tests have shown that, for example, a visibility threshold of a diameter defect exists at 400 cm %. In accordance with a threshold value of 400 cm %, for example, a shutdown is initiated if there are long defects which, with a length of 40 cm, have a diameter increase of more than 10% or, with a length of 10 cm, have a diameter increase of more than 40%. Moreover, any other diameter increase and length is possible if the product thereof results in a value of or exceeds 400 cm %.

Mathematically speaking, in the sliding calculation of average values of the yarn profile deviation, each averaged profile deviation in percent is calculated at each measuring point according to the following formula, which is simply the arithmetic mean of the deviation of the standardized yarn diameters included in the respective average:

$$Y_{fj} = Y_{f(j-1)} + [(Y_{Aj} - Y_{F(j-1)})/j]$$

where:

$Y_{fj}$ = the calculated average profile deviation in %, $Y_{F(j-1)}$=the last calculated averaged profile deviation in %, $Y_{Aj}$=the standardized yarn diameter in %, and j=the number of measuring points included in the calculation.

For conversion of a measured yarn diameter at measuring point j into the percent value $Y_{Aj}$, the yarn diameter is multiplied by the standardization factor N which equals 100 %/r, where r is the reference yarn diameter in mm.

The threshold value used with the average value calculation must take into account the relation between the defect length and the defect size. This is achieved by means of the threshold deviation function:

$$f(j)=[\text{(allowed threshold value [cm \%]}\cdot 10 \text{ [mm/cm])/measurement resolution [mm/scanning points]}]/j[\text{scanning points}]$$

where j is the number of measuring points and the measurement resolution is the distance between measuring points which depends upon the resolution of the sensor that measures the yarn diameter.

The calculation of respective totals of the values of the profile deviations for each section and each sequence measured (the integration calculations) occurs in accordance with the second evaluation technique wherein the deviation of standardized measured yarn diameters are continuously added together and the sum assigned to the appropriate measuring point in accordance with the following formula:

$$Y_i=Y_{(i-1)}+(Y_{Ai}-100)$$

where:

$Y_i$=calculated total of the values of the profile deviations in %, $Y_{(i-1)}$=total of the values of the profile deviations of the previous measurement in %, $Y_{Ai}$=standardized yarn diameter in %, and i=the number of measuring points in the measuring area of the yarn.

The result must be compared with a threshold value G which is associated with the yarn section being checked, and if a calculated total value of the profile deviation times the number of measuring points i exceeds the threshold value G, a yarn defect is detected. In this formula the threshold value G of each section is preferably fixed. Note also that the section-specific threshold value G has been converted from the normal dimensions [cm %] to the dimensions [%·scanning points] in accordance with the following conversion formula: G=(the desired threshold value [cm %]·10 [mm / cm]) / (measurement resolution [mm/scanning points]).

Thus, with respect to the second evaluation technique of integral formation, a fixed threshold value is compared to a comparison value representing the product of a measured value and the yarn length, or the number of measuring points, whereas with regard to the first evaluation technique, a threshold value curve is compared to a comparison value representing a sliding average value formation which takes the number of measuring points and corresponding measurements into consideration as well as the average value formation thereof. Moreover, there is a decreasing effect of each measurement of each measuring point on the average value formation as the distance from the starting measuring point of the average value formation increases.

Figure 2:
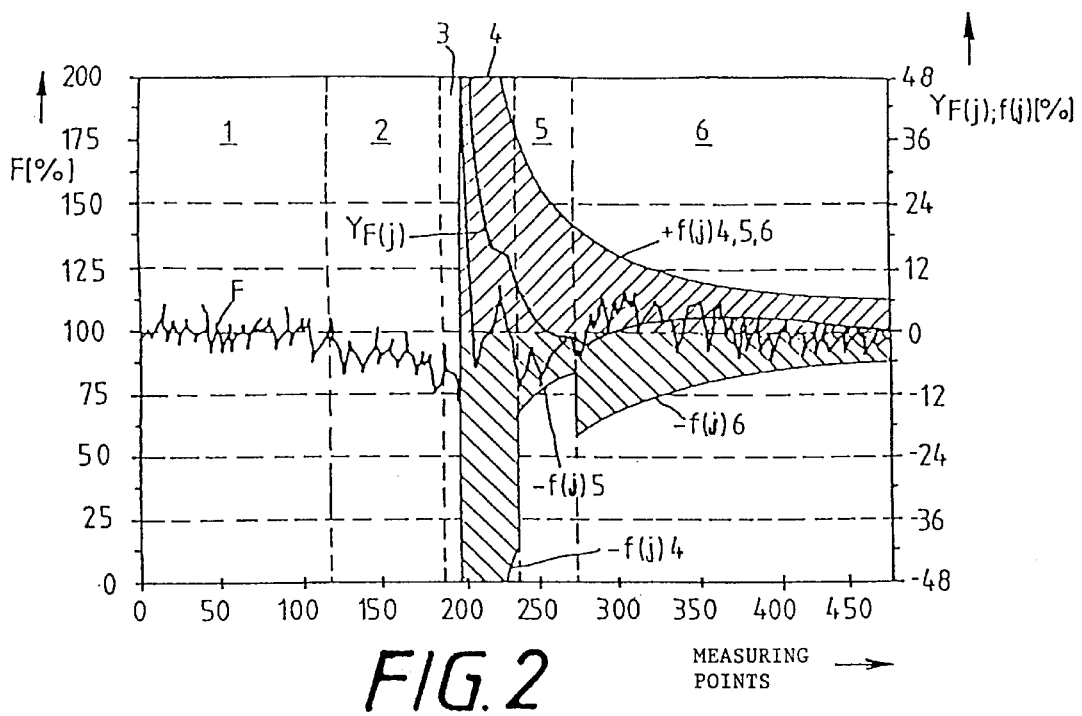
FIG. 2 shows an evaluation of a yarn profile in accordance with a first evaluation technique of the first featured method of the present invention.
Figure 3:
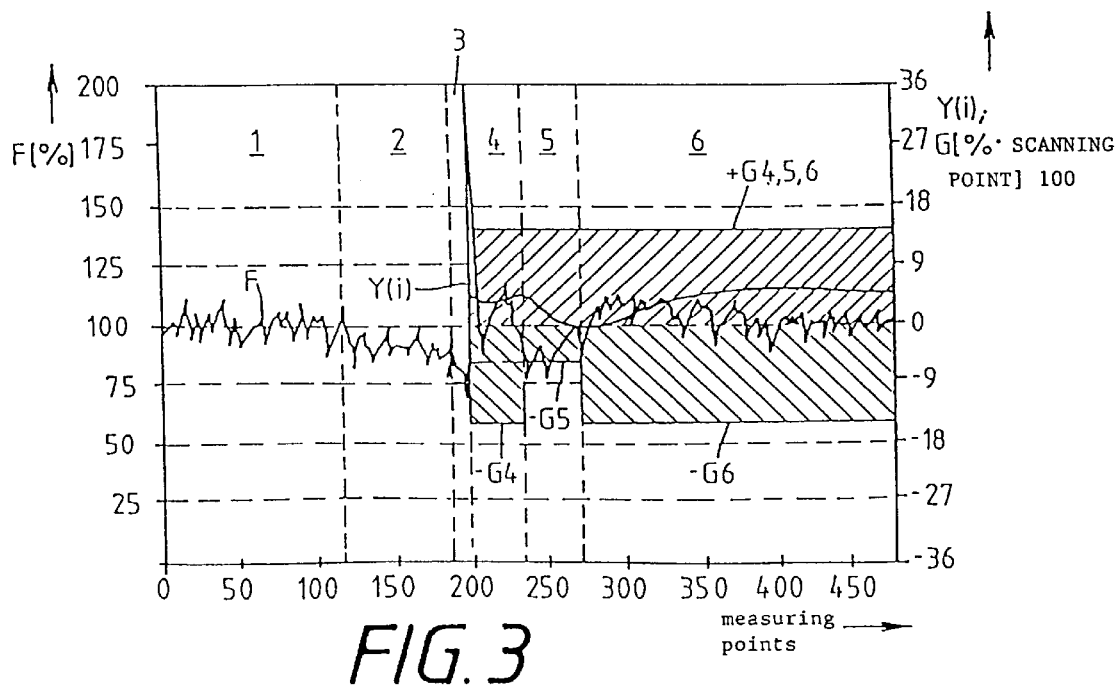
FIG. 3 shows another evaluation of a yarn profile in accordance with a second evaluation technique of the first featured method of the present invention.

Application of these two evaluation techniques, or evaluation protocols, with respect to the first featured method of the present invention are represented in FIGS. 2 and 3, where in FIG. 2 the evaluation of the yarn is performed in accordance with the first evaluation technique, and where in FIG. 3 the evaluation of the yarn is performed in accordance with the second evaluation technique.

It should be noted that, in both cases, an evaluation which extends past the pieced section 4 is performed in order to detect thick or thin places which possibly extend without a change in sign past the sectional boundaries of sections 4 and 5. However, in accordance with the present invention, an independent measurement evaluation is simultaneously started at each new sectional boundary which is not shown in FIGS. 2 and 3 for clarity of illustration. In this connection, reference is made to FIGS. 4a and 4b discussed below.

The yarn profile of FIGS. 2 and 3 include a tested yarn length of 450 measuring points and start at the upper yarn, which is tested over a length of 320 mm for the determination of a reference value for the yarn profile following piecing. The length of the tested yarn section is respectively plotted in the coordinate system on the abscissa by means of the number of the measured measuring points, and the number of the measuring points must be multiplied by the measuring resolution in order to determine the actual test length. The diameter measurement curve F detected by the yarn testing sensor is substantially identical in both FIGS. 2 and 3.

In the preferred method of the present invention, the check of the yarn profile by the two evaluation protocols as shown in FIG. 2 and FIG. 3 begins with the pieced section 4. This check of the yarn profile is made both in respect to short and long thick places and thin places. In both cases, the threshold values have been entered on both sides of the normal yarn diameter of 100% which, in FIG. 2, should not exceed the profile deviations slidably determined in accordance with the first formula discussed above and, in FIG. 3, the total values of the profile deviations times the yarn length (in measuring points) in accordance with the second formula discussed above.

It can be seen from FIGS. 2 and 3 that the same thresholds $+f_{(j)\,4,\,5,\,6}$ or $+G_{4,\,5,\,6}$ for short deviations and for tendencies toward upper deviations from the diameter have been respectively set in the pieced section 4, in section 5 following the pieced section 4, and in section 6 following section 5. For short thin places and for tendencies toward lower deviations from the diameter, the same threshold $-f_{(i)4}$ and $-f_{(i)6}$ or $-G_4$ and $-G_6$ have also been selected in the areas in the pieced section 4 and in the section 6 following section 5 in FIGS. 2 and 3. The desired threshold value respectively preferably corresponds to 400 cm %. Only in section 5 following the pieced section 4 has a different desired threshold value been selected for both measuring protocols for thin places, so that a different threshold value curve $-f_{(i)5}$ or $-G_5$ is created. The desired threshold value here respectively preferably corresponds to 150 cm %. Depending on the spinning parameters, spinning means, and mainly the settings of the piecing unit, it is possible that thin places or thick places occur in the section 5 following the pieced section 4. In this area the thin places cause a clear reduction of the yarn strength. Therefore, the taking into consideration of the two quality characteristics of strength and visual impression of the yarn require different thresholds in this area, and threshold values corresponding to 150 cm % have therefore been selected for $-f_{(1)5}$ and $-G_5$.

It can be seen from both measuring protocols in FIGS. 2 and 3 that both the curve $Y_{F(j)}$ of the slidably determined profile deviations and the curve of the product of $Y_{(i)}$ and the yarn length i (hereinafter Y(i)) extends within the thresholds and nowhere equals or exceeds the threshold values.

Figure 4A:
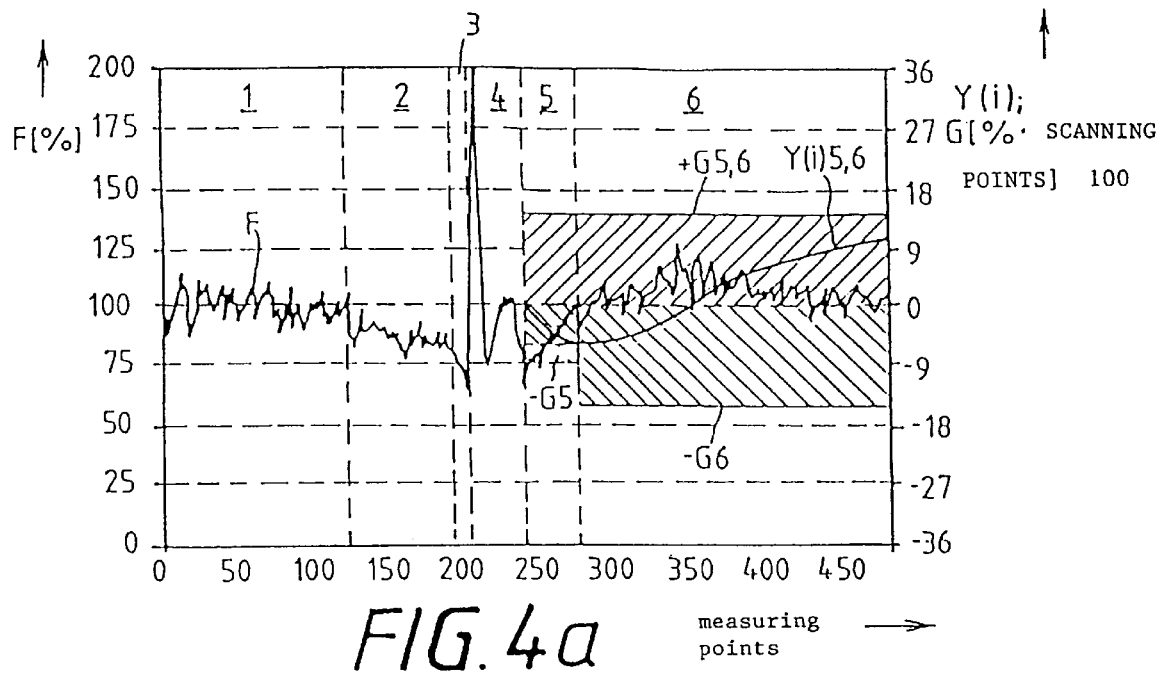
FIG. 4a shows an evaluation of multiple sections of a yarn profile in accordance with the second evaluation technique over the first featured method of the present invention.
Figure 4B:
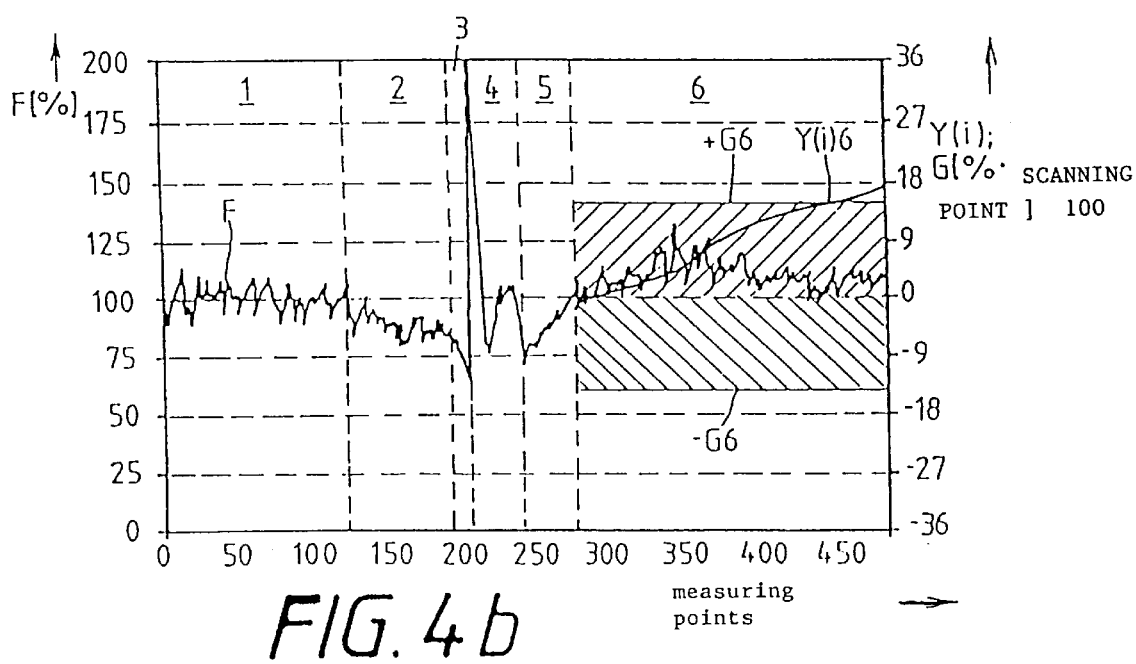
FIG. 4b shows an evaluation of one section of a yarn profile in accordance with the second evaluation technique of the first featured method of the present invention.

In accordance with a characteristic of the first featured method of the present invention, the second evaluation technique is used over different sections in FIGS. 4a and 4b which both relate to yarn profile F. In the common evaluation of a thin place in the section 5 following section 4, and in an impermissibly long thick place in section 6 following section 5 as represented in the measuring protocol of FIG. 4a, the curve $Y(i)_{5,6}$ is still located within the predetermined thresholds $+G_{5,6}$ as well as $-G_5$ and $-G_6$. The defect is only detected if the evaluation of the yarn profile in the section 6 following section 5 is performed separately from section 5, as represented in FIG. 4b. The curve of the total values of the profile deviations $Y(i)_6$ which is only related to the section 6 following section 5 intersects the predetermined threshold $+G_6$ and indicates that an impermissibly thick place is present.

While not presently shown, the threshold determination for long defects in section 3 with respect to other sections should be reduced, for example, to 200 cm % from 400 cm %. This threshold reduction in section 3 occurs since, on the one hand, an also already short thin place in the section 3 affects the piecing strength and, on the other hand, for threshold values determined on the basis of visual viewpoints for long defects the area is too short to cause a shutdown.

Finally, with regard to point-sized deviations, since there is a clear reduction of the piecing strength if the diameter is even slightly lower in section 4, as compared to other sections, the threshold value of a short thin place in section 4 is set considerably lower to, for example, −5% compared with, for example, −50%.

The second featured method of the present invention includes the determination of fiber or trash accumulation which has remained in the rotor and which has come to reside in the pieced yarn section itself as a thickening of the yarn in this section. Such a determination is not possible by the known methods of the prior art because of the structure of the pieced yarn section, which greatly fluctuates from a standard yarn but which fluctuations are acceptable in yarn processing.

Specifically, if the yarn cross section of the pieced section is represented over its length, a more or less distinctive letter "M" generally results. This is essentially created in that, starting at the connection point, a first overlapping area between the upper yarn end and the newly pieced fibers is created, which locally increases the thickness and the mass of the yarn. This peak, which is normally the absolute maximum, is followed by a reduction in the yarn cross section to approximately the standard yarn thickness. This is followed by a larger fiber accumulation whose measured value peak is less than the first peak. This fiber accumulation is caused because, on the one hand, at the start of the yarn draw-off during the piecing operation a fiber ring must be present in the rotor groove, which must be of sufficiently distinctive thickness so that no thin place in the yarn occurs after overlapping at the connection point which would cause reduced strength of the pieced section, and, on the other hand, it is necessary to feed sufficient fibers even during the draw-off of the first yarn length corresponding to the rotor circumference (pieced section) in order not to result in a very distinctive thin place downstream of the pieced section. These fibers, which are continuously fed to the first fiber ring length during the draw-off generate the described second thick place in the pieced section.

Preferably, the evaluation of the pieced yarn section is advantageously performed in accordance with the invention in three subsections of the pieced yarn section, where in the first and third subsections the yarn thickness increase associated with non-defective pieced sections is found. Fluff is detected in either of these subsections if a clearly local thickness increase exceeding the respective normal increase is detected. In this process it is possible to form an average value of the measured values over the respective first and third subsections and to compare the values with a single threshold value for each subsection, or alternatively, to monitor for a measured value which exceeds a respective threshold value.

With respect to the second or middle subsection, the yarn diameter recedes locally to approximately the standard yarn length in the center area of the pieced yarn section and it is also possible that deviations which can be tolerated occur here from one pieced section to the next pieced section. The detection of fluff or sloughing or trash accumulation in this subsection requires an evaluation which differs from the other subsections. In this case it must also be taken into consideration that in its length this subsection is a multiple of the other subsections. Accordingly, fluff would, for example, not affect the average value of the second subsection as gravely as in the other two subsections. In the same way, a thin place superimposed on the fluff could compensate the thick place caused by fluff in such a way that a single measurement evaluation as well as an average value formation would not result in exceeding the threshold value for detection of fluff.

For this reason, the detection of a rise and subsequent drop of the yarn thickness or the yarn mass, which is relatively rapid in respect to the length of the second subsection, is advantageously used for detecting fluff in this area. This can take place, for example, in that the respective actually measured yarn value is compared with yarn values immediately ahead and behind it, wherein the distance of the actually measured yarn value from the measured value used for comparison should advantageously be selected to be large enough so that fluff dimensions which are to be expected, depending on the fiber material and the spinning means, are approximately included in respect to their longitudinal extent. Effects of the yarn nappiness in particular should be suppressed in this connection. A threshold value for the fluff-related diameter increase is of course also set and results from a maximally tolerable measured value difference between the actual measured value and the adjoining measured values which are used for the comparison.

An essential importance is also given to the position of fluff in the pieced yarn section. Thus, fluff in one of the edge areas is important both in respect to the visual quality and strength of the yarn. With respect to FIG. 5, the fluff-related adjoining thin place therefore has a particular strength-reducing effect if it falls in the area 4b. This is also the case when the fluff is located in the area 4c. Its detection as a thick place and its removal is assured because of a very high threshold value having been exceeded. However, because of the neighboring twist-connected thin place there, false regulations of the piecing device can also occur if it is not recognized that this is fluff and therefore a defect that cannot be corrected for by altering controlled variables of the piecing operation. In contrast thereto, as a rule the recognition of it as a thick place by means of conventional pieced section test methods is not possible in the center area because of the yarn thickness. Fluff in this area also leads to a relatively large reduction of the yarn strength because of an adjoining thin place, especially if in the running direction of the yarn the fluff is located directly behind the yarn profile value which is independent of fluff.

In order to assure that fiber or trash accumulations located in the subsectional boundaries are also detected as such, it is advantageous to preset an overlap of the subsectional boundaries. In this case, attention must be paid to the selection of the extent of the subsection in such a way that the respective area-specific evaluation can be successfully performed. The determination of the subsectional boundaries can take place as a function of the spinning means and the fiber material to be processed, wherein this setting is performed particularly advantageously if, following the first pieced section of the batch, information regarding the average structure of the above mentioned "M" is available.

Figure 5:
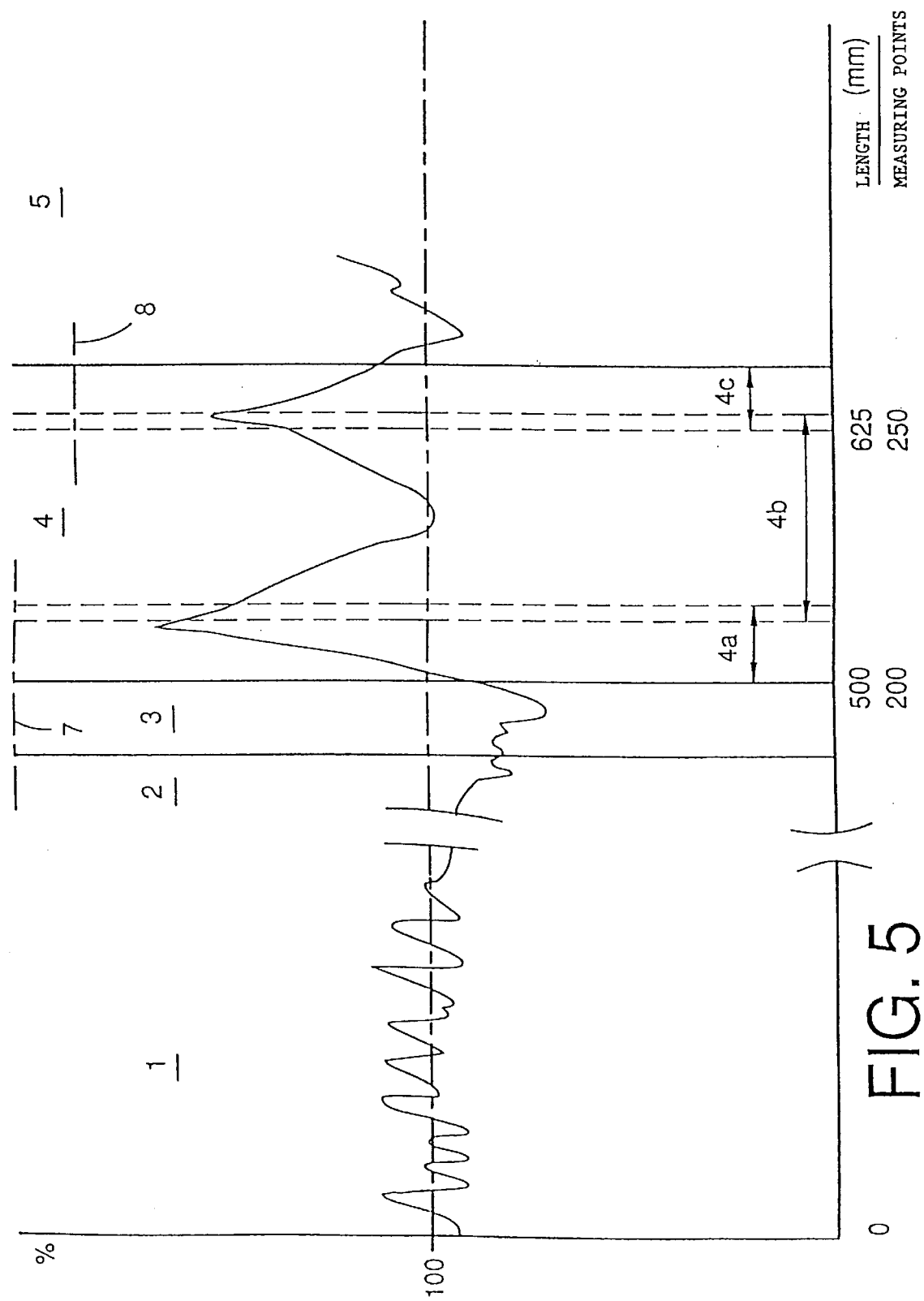
FIG. 5 shows a typical yarn profile of a pieced yarn section as well as adjoining sections.

Referring now to FIG. 5 in detail, the pieced section 4 has been divided into three subsections 4*a*, 4*b* and 4*c*. Subsection 4*a* includes the overlap length between the yarn end and the pieced fibers and therefore forms a local thickening of the yarn. The thickening in subsection 4*c* is created by the addition of the fibers, already described above. Subsection 4*b* extends over the predominant portion of the pieced section 4 between subsections 4*a* and 4*c*.

While subsections 4*a* and 4*c* are distinguished by initially increasing and then, after reaching a maximum, decreasing measured values of the yarn diameter, subsection 4*b* is distinguished by a reduction and subsequent increase of the yarn diameter, with all three subsections respectively overlapping neighboring subsections. Because of this it is possible to detect fluff, trash accumulations and sloughing located at the subsectional boundaries.

Threshold values 7 and 8 for subsections 4*a* and 4*c* are shown in FIGS. 5–8, for which single deviations are monitored. These threshold values have been fixed in such a way that, if they are exceeded once, then a defect is detected. It is also possible to form an average value over the respective subsections, which would then correspond to threshold values established below the shown threshold values.

Figure 6:
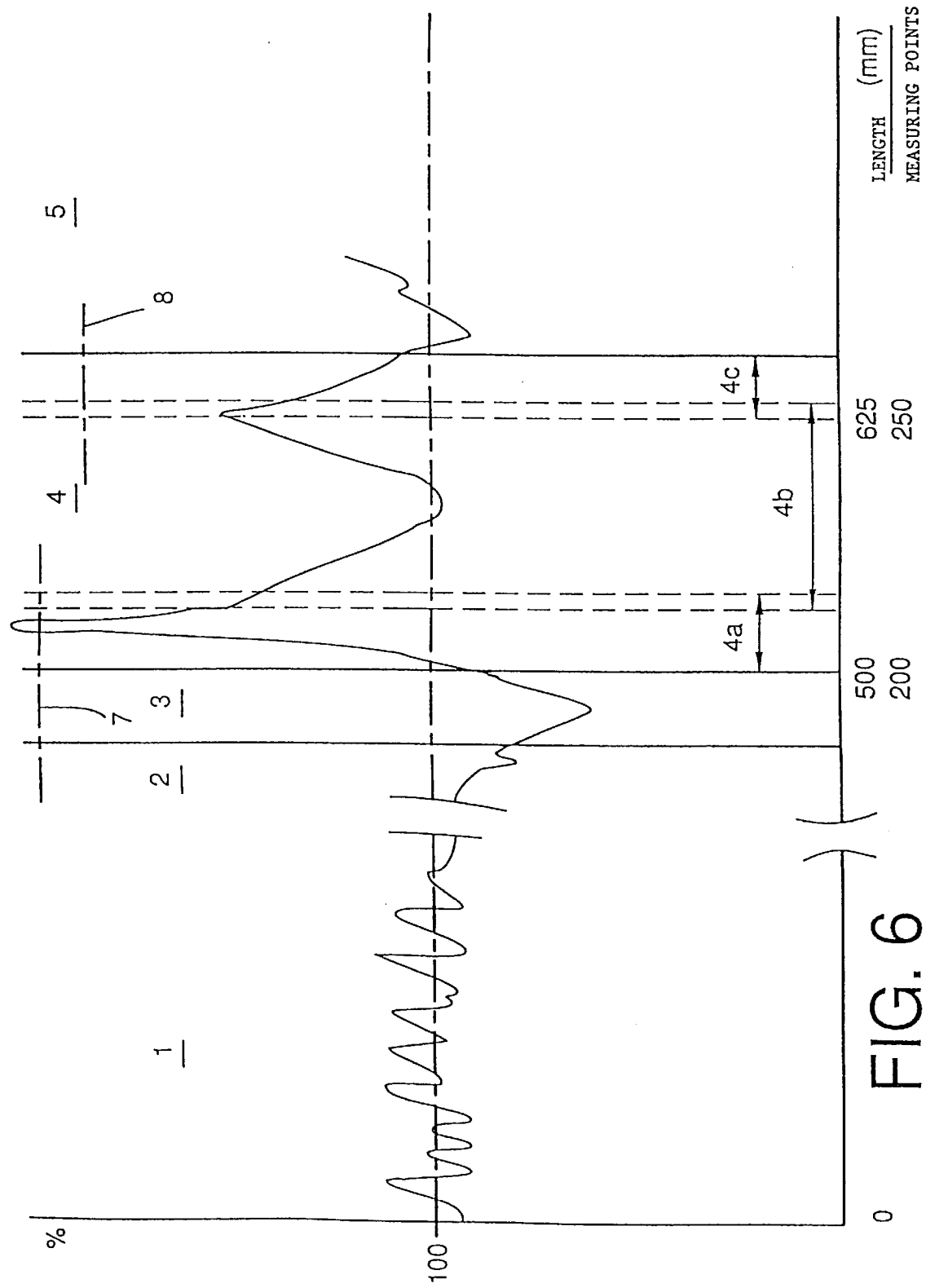
FIG. 6 shows a yarn profile having fluff incorporated in the direct neighborhood of the yarn connection point.
Figure 7:
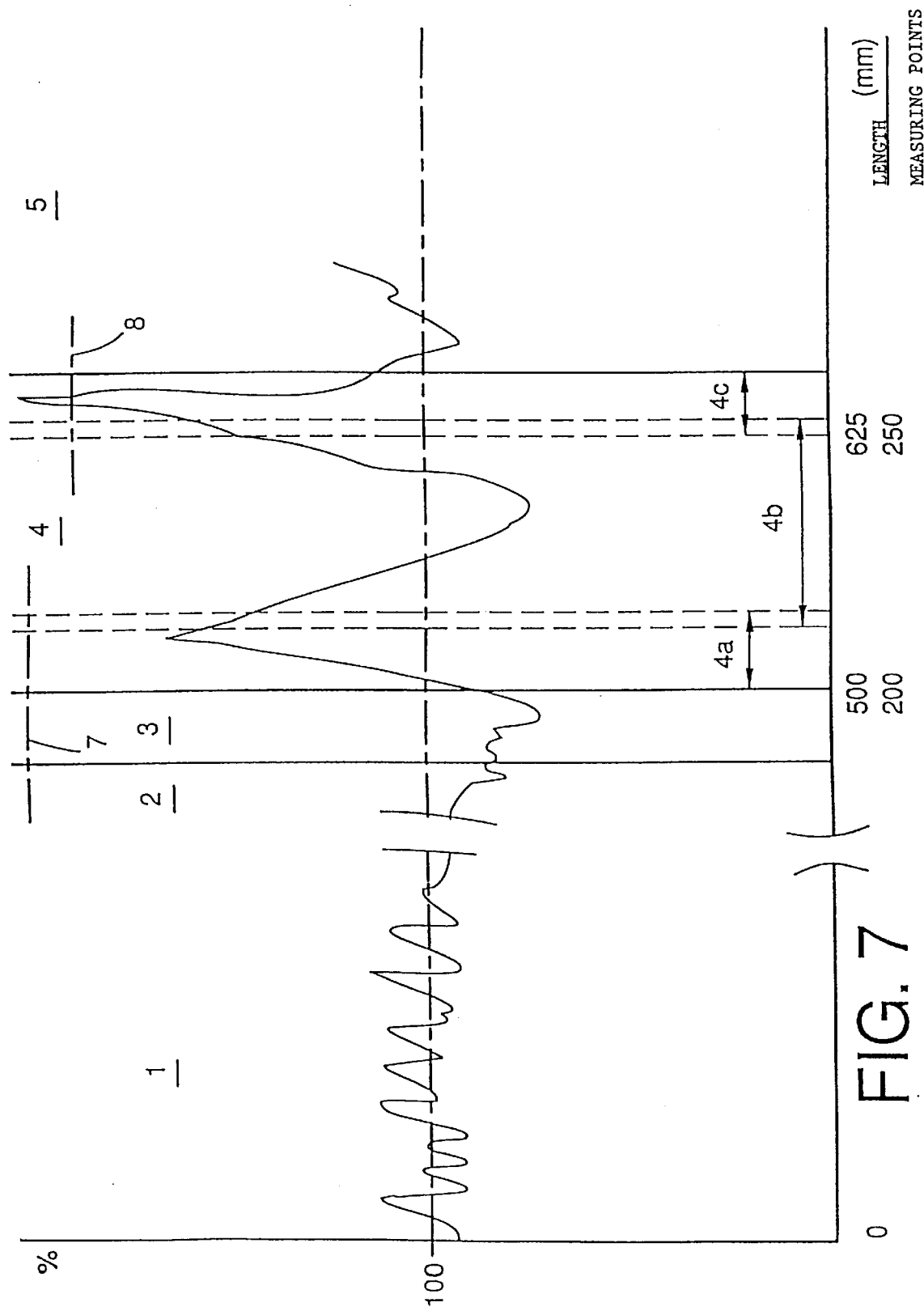
FIG. 7 shows a yarn profile analogous to FIG. 5, but with yarn sloughing formed toward the end of the pieced yarn section.

Threshold values which have been exceeded in subsections 4*a* and 4*c* are represented in FIGS. 6 and 7. As can be seen in FIG. 6, the act of exceeding the threshold value 7 indicates a further reduction of the yarn diameter in the neighboring section 3. This further reduction of the yarn diameter in section 3 would, if the fluff formation in subsection 4*a* had not been detected, cause a correction of the coefficient of rotation for the piecing device, although the fluff which appeared here has no connection with a faulty coefficient of rotation. The result of the prior art methods in such a situation would be the reduction of the coefficient of rotation during subsequent piecing processes, which would result in a pieced section with insufficient twisting and therefore also reduced strength. In addition to avoiding such false regulation of the piecing operation, it is possible with the present invention to signal such fluff formation, trash accumulation and sloughing at the respective spinning station to the operators, so that the required steps can be initiated in a directed manner to correct the actual cause of the defect. Among these is, for example, the clearing of the valve bore in the fiber conduit plate or, in connection with sloughing, the changing of the draw-off nozzle, if necessary.

In FIG. 7 sloughing is detected in subsection 4*c*, which indicates a thin place in the preceding subsection 4*b* and leads to a strength reduction of the yarn. However, it is noted that the evaluation of sloughing takes place in the same way as the evaluation of fluff It is therefore necessary in case of a local accumulation of fibers to investigate the reason for the defect. Otherwise the same evaluation principles apply here as already explained in connection with FIG. 6.

Figure 8:
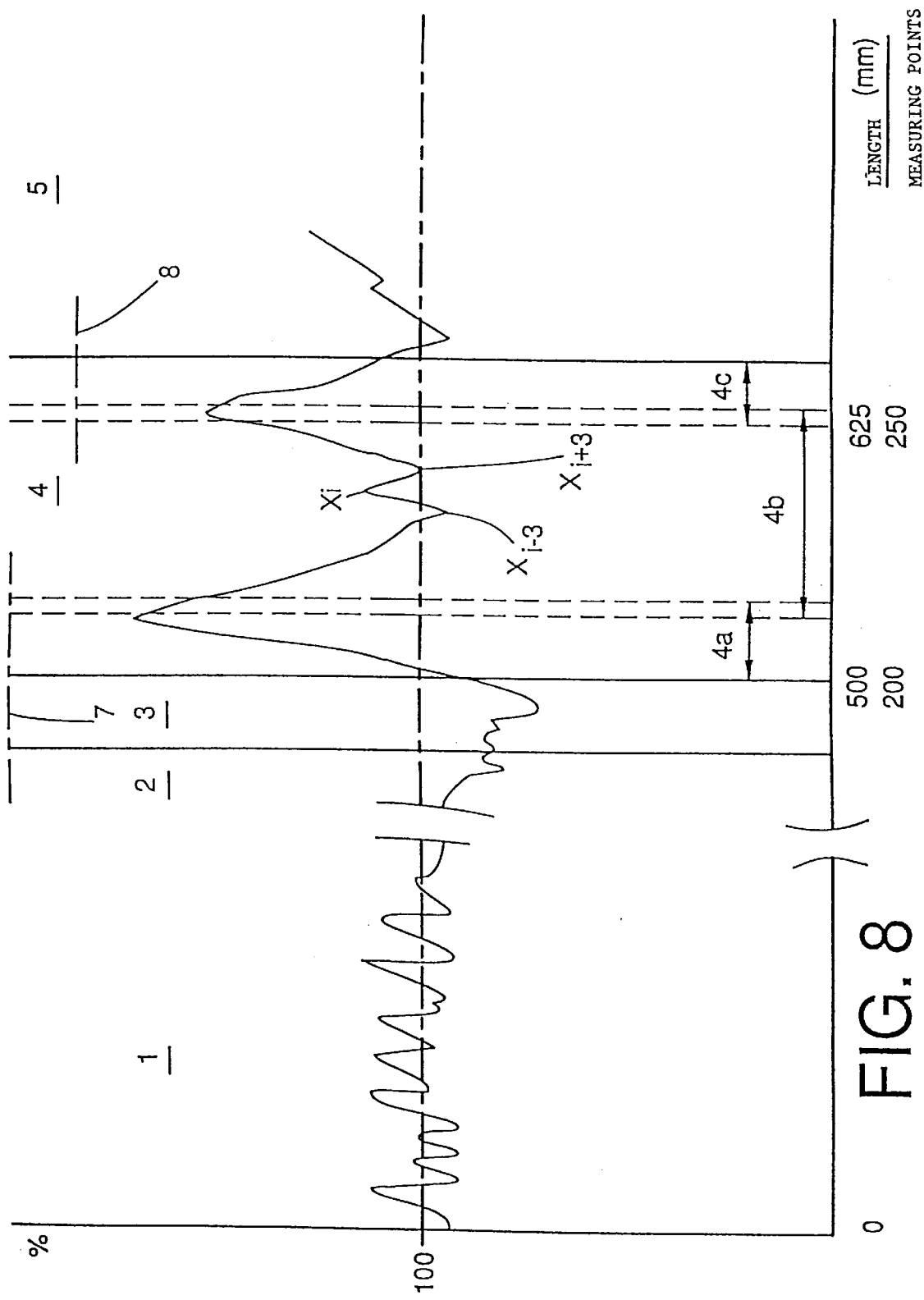
FIG. 8 shows a yarn profile analogous to FIG. 5, but with trash accumulation incorporated into the center of the pieced yarn section.

A fiber or trash accumulation in subsection 4*b* is represented in FIG. 8. It can be seen here that the extent of this defect in respect to the yarn diameter still clearly falls below the value of the neighboring thick places which occur in the normal pieced section. For this reason, it is difficult to detect this defect by means of average value formation or monitoring of absolute values and comparison thereof with a threshold value. For this reason, a respective comparison of the actual measured value with adjacent threshold values is performed in order to be able to detect a flank rise or a flank drop in the neighborhood of this measured value. If, for example, the actual measured value $X_i$ has reached the peak value caused by a defect, the average diameter values detected to the left and right of this value, for example $X_{i-3}$ and $X_{i+3}$, are clearly located below the actual measured value. In the present case, i.e., at a measuring resolution of 2.5 mm, the distance of the measured values included in addition to the actual value from the actual average value is respectively 7.5 mm. This comparison of the measured values is performed across the entire subsection 4*b*, wherein fluff detection occurs when the measured values considered to the left and right of the actual measured value are clearly below the actual measured value. It is possible in this way to localize the defect, for example fluff, in a very good way, based on such a local maximum.

In this connection it should also be noted that the distance of the measuring values to the left and right of the actual measured value and included in the evaluation can be changed, wherein too close a distance can lead to false evaluation because of the nap of the yarn, while too great a distance negates the detectability of the defect in those cases where the influence of the normal yarn profile is dominant. It should also be noted that because of the twist-related thin place the left flank is extended.

The determination of tendencies of yarn profile deviations and the exact determination of each yarn section's location, which is clearly improved by means of the present invention, also permits the evaluation of the pieced sections in which defect tolerances have not been exceeded. In contrast to the inclusion of only defective pieced sections in the evaluation and control of the piecing conditions, it is possible because of this to clearly and more quickly obtain improved results in spinning and piecing operations.

It will therefore be readily understood by those persons skilled in the art that the present invention is susceptible of a broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention.

What is claimed is:

1. A method for checking a yarn for yam defects following a piecing operation in an open-end spinning machine, comprising:
   a. drawing off the yarn from the spinning machine following the piecing operation during which a connection point is formed between a returned yam and a newly spun yarn;

b. determining with a sensor deviations in a yarn profile of the yarn being drawn off from a yarn profile of a yarn that is unaffected by a piecing operation and storing said deviations in a computer;

c. identifying with said computer for evaluation purposes a plurality of yarn sections corresponding to said determined deviations, at least one said section beginning at said connection point; and d. evaluating for yarn defects by calculating with said computer a comparison value for each said deviation determined in each said section and by comparing said comparison values with threshold values that are predetermined by permissible deviations from the unaffected yarn profile and that are specific to each said section, a defect being evaluated if any comparison value in a section transgresses the threshold value for that section.

2. The method according to claim 1, further comprising the step of determining the cause of an evaluated defect based upon the type and location of the defect thereby determining information for evaluating possible modification of the piecing operation.

3. The method according to claim 1, wherein said identifying and said determining further include determining with the sensor deviations in the yarn profile before the piecing operation and identifying the location of said connection point by determining a maximum measured yarn diameter within a yarn area in which the connection point is expected and then locating a first measured yarn diameter occurring before said maximum measured yarn diameter that is less than a standard yarn diameter of the unaffected yarn.

4. The method according to claim 1, further including the identifying of at least five sections including a pieced section and two sections respectively located in front of and behind said pieced section, said pieced section beginning at said connection point and extending along the yarn from said connection point over a length corresponding to a rotor groove circumference of the spinning machine.

5. The method according to claim 1, wherein said identifying with said computer includes determining the length of each said section as a function of the geometry of the spinning machine and yarn parameters.

6. The method according to claim 1, wherein each said calculation of the comparison value for each said determined deviation in each section is a function of all determined deviations occurring in said section prior to and including said deviation for which said comparison value is calculated.

7. The method according to claim 1, wherein each said calculated comparison value for each said determined deviation in each section represents the product of the sum of the deviations occurring in said section prior to and including said deviation for which said comparison value is calculated and the number of the deviations comprising said sum, whereby a defect is detected if said comparison value transgresses a predetermined fixed threshold value.

8. The method according to claim 1, wherein each said calculated comparison value for each said determined deviation in each section represents an average deviation over deviations occurring in said section prior to and including said deviation for which said comparison value is calculated, whereby a defect is detected if said comparison value transgresses a threshold value representing a predetermined value for said section divided by the number of deviations averaged in said comparison value.

9. The method according to claim 1, further including the determining with said computer of each said threshold value by taking into consideration a predetermined required yarn strength in the individual sections and the capability of detecting defects in yarn products during further processing.

10. The method according to claim 1, further including the continuing of each said evaluation begun in at least one of said sections into another one of said sections independently of the start of a said evaluation in said following section.

11. The method according to claim 1, further including retaining and accumulating in said computer said comparison values calculated for a plurality of piecing operations, regardless of whether a defect is detected, for detecting yarn tendencies.

12. The method in according to claim 1, further comprising determining the standard yarn profile from a top yarn which first passes said sensor after the start of the yarn draw-off in the course of the piecing operation and which is unaffected by the piecing operation.

13. A method for checking a yarn for yarn defects following a piecing operation in an open-end spinning machine, comprising the steps of:

a. drawing off the yarn from the spinning machine following the piecing operation during which a connection point is formed between a returned yarn and a newly spun yarn;

b. determining with a sensor deviations of a yarn profile of the yarn being drawn off from a yarn profile of a yarn that is unaffected by a piecing operation and storing said deviations in a computer;

identifying with said computer for evaluation purposes a pieced section of the yarn beginning at said connection point and extending thereafter on the yarn over a length corresponding to one circumference of a rotor groove of the spinning machine;

d. further identifying with said computer for evaluation purposes a plurality of subsections comprising said pieced section; and e. evaluating the pieced section for yarn defects by making a subsection-specific evaluation of said deviations in each said subsection.

14. The method according to claim 13, wherein said identifying with said computer includes the identifying three subsections of said pieced section.

15. The method according to claim 14, wherein said evaluating includes detecting defects by comparing said deviations in two said subsections which include the boundaries of said pieced section to respective threshold values, and by detecting a sequence of flank rises and drops in the deviations in a third said subsection located between said two subsections.

16. The method according to claim 13, wherein said identifying with said computer includes the determining of the length of said pieced yarn section as a function of the geometry of the spinning machine and yarn parameters.

17. The method according to claim 13, wherein the boundaries of said subsections overlap.

18. A method for checking a yarn for yarn defects following a piecing operation in an open-end spinning machine, comprising:

(a) drawing off the yarn from the spinning machine following the piecing operation during which a connection point is formed between a returned yarn and a newly spun yarn;

(b) determining with a sensor deviations of a yarn profile of the yarn being drawn off from a yarn profile of a yarn that is unaffected by a piecing operation and storing said deviations in a computer, said determining of said deviations occurring before, when, and after said connection point passes said sensor;

(c) identifying with said computer for evaluation purposes at least three yarn sections corresponding to said deviations determined when and after said connection point passes said sensor, at least one said section being a pieced section and beginning at said connection point, and further identifying three subsections comprising said pieced section;

(d) evaluating for yarn defects by:
  (i) calculating for each deviation in each section a comparison value representing the product of the sum of the measured deviations occurring in said section prior to and including said deviation for which said comparison value is calculated and the number of deviations comprising said sum, whereby a defect is detected if said comparison value transgresses a predetermined fixed threshold value for said section.
  (ii) calculating for each deviation in each section a comparison value representing an average deviation over measured deviations occurring in said section prior to and including said deviation for which said comparison value is calculated, whereby a defect is detected if said comparison value transgresses a threshold value representing a predetermined value for said section divided by the number of deviations averaged in said comparison value, and
  (iii) continuing each said evaluation into other said sections independently of the start of a said evaluation in another said section; and (e) further evaluating for yarn defects in said pieced section:
  (i) by comparing said deviations determined in two said subsections which include the boundaries of said pieced section to respective threshold values, whereby a defect is detected if a said deviation transgresses a threshold value, and
  (ii) by detecting a sequence of flank rises and drops in the yarn profile in a third said subsection located between said two subsections.

19. A method according to claim 18, further including determining with said computer the cause of an evaluated defect based upon the type and location of the defect thereby providing information for evaluating possible modification of the piecing process.

20. A method for checking a yarn for yarn defects following a piecing operation in an open-end spinning machine, comprising:

a. drawing off the yarn from the spinning machine following the piecing operation during which a connection point is formed between a returned yarn and a newly spun yarn;

b. determining with a sensor deviations in a yarn profile of the yarn being drawn off from a yarn profile of a yarn that is unaffected by a piecing operation and storing said deviations in a computer;

c. identifying with said computer for evaluation purposes a plurality of yarn sections corresponding to said determined deviations; and d. evaluating for yarn defects by calculating with said computer a comparison value for each said deviation determined in each said section, each said calculation being a function of all determined deviations occurring in said section prior to and including said deviation for which said comparison value is calculated, whereby a defect is detected if a comparison value transgresses a section-specific threshold value.

* * * * *